United States Patent
Ohshita

(10) Patent No.: US 11,439,147 B2
(45) Date of Patent: Sep. 13, 2022

(54) 3-PYRIDYL OXYANILINE COMPOUND AND USE OF SAME

(71) Applicant: Sumitomo Chemical Company, Limited, Tokyo (JP)

(72) Inventor: Jun Ohshita, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 871 days.

(21) Appl. No.: 16/328,084

(22) PCT Filed: Aug. 24, 2017

(86) PCT No.: PCT/JP2017/030249
§ 371 (c)(1),
(2) Date: Feb. 25, 2019

(87) PCT Pub. No.: WO2018/038191
PCT Pub. Date: Mar. 1, 2018

(65) Prior Publication Data
US 2019/0183122 A1      Jun. 20, 2019

(30) Foreign Application Priority Data

Aug. 26, 2016  (JP) ................................. 2016-165425
Oct. 27, 2016  (JP) ............................. JP2016-210330

(51) Int. Cl.
*A01N 43/40*       (2006.01)
*C07D 213/69*    (2006.01)

(52) U.S. Cl.
CPC ........... *A01N 43/40* (2013.01); *C07D 213/69* (2013.01)

(58) Field of Classification Search
None
See application file for complete search history.

(56) References Cited

U.S. PATENT DOCUMENTS 6,537,948 B1      3/2003   Tohyama et al.

FOREIGN PATENT DOCUMENTS

JP     1356247 B2      11/2009
WO   2007083090 A2    7/2007

OTHER PUBLICATIONS

English Translation of International Preliminary Report dated Feb. 26, 2019 in International Application No. PCT/JP2017/030249.
English Translation of International Search Report dated Oct. 10, 2017 in International Application No. PCT/JP2017/030249.

*Primary Examiner* — Alton N Pryor
(74) *Attorney, Agent, or Firm* — Panitch Schwarze Belisario & Nadel LLP

(57) ABSTRACT

Provided is a compound represented by formula (1):

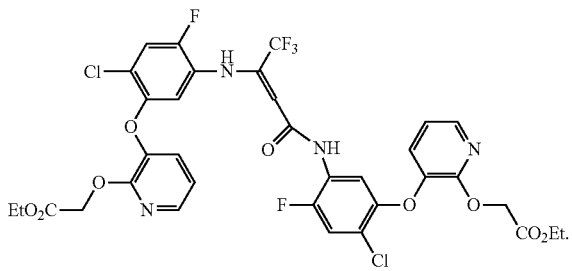

(1)

The compound represented by formula (1) has an excellent efficacy for controlling weeds, and is thus useful as an active ingredient for an agent for controlling weeds.

3 Claims, No Drawings

3-PYRIDYL OXYANILINE COMPOUND AND USE OF SAME

CROSS-REFERENCE TO RELATED APPLICATION

This application is a Section 371 of International Application No. PCT/JP2017/030249, filed Aug. 24, 2017, which was published in the Japanese language on Mar. 1, 2018 under International Publication No. WO 2018/038191 A1, which claims priority under 35 U.S.C. § 119(b) to Japanese Application No. 2016-165425, filed Aug. 26, 2016, and Japanese Application No. 2016-210330, filed Oct. 27, 2016, the disclosures of which are incorporated herein by reference.

TECHNICAL FIELD

The present invention is related to a 3-pyridyl oxyaniline compound and a use of the same.

BACKGROUND ART

Patent document 1 describes 4-chloro-2-fluoro-5-{2-(ethoxycarbonyl)methoxy-3-pyridyloxy}aniline, and N-[4-chloro-2-fluoro-5-(2-(ethoxycarbonyl)methoxy-3-pyridyloxylphenyl]-trifluoroaceto acetic acid amide.

CITATION LIST

Patent Document

Patent Document 1: JP patent No. 4356247 B2

SUMMARY OF THE INVENTION (Problems to be Solved by Invention)
An object of the present, invention is to provide a compound having an excellent efficacy for controlling weeds.
(Means to Solve Problems)
The present inventor has intensively studied to solve the problems, and as a result, he found out that a compound represented by the following formula (1) has an excellent control efficacy on weeds.
That is, the present, invention includes the followings.
[1] A compound represented by formula (1):

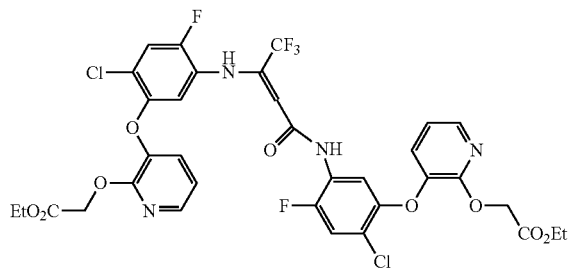

(1)

(hereinafter, referred to as "Compound of the present invention" or "Present compound").

[2] A herbicide comprising the compound described in [1](hereinafter, referred to as "Herbicide of the present invention" or "Present herbicide").

[3] A method for controlling a weed which comprises applying the compound described in [1] to the weed or soil where the weed is growing.

[4] Use of the compound described in [1] to control a weed,

[Effect of Invention]

The compound of the present invention has an excellent efficacy for controlling weeds, and is thus useful as an active ingredient for a herbicide.

Mode for Carrying out the Invention

The herbicide of the present invention comprises a compound of the present invention and an inert carrier. Examples of the inert carrier include a solid carrier and a liquid carrier. The herbicide of the present invention is usually prepared by further adding the other auxiliary agents for formulation such as surfactants, stickers, dispersers, and stabilizers, to formulate into wettable powders, water dispersible granules, suspension concentrates, granules, dry flowables, emulsifiable concentrates, aqueous solutions, oil solutions, smoking agents, aerosols, microcapsules and the others. In the herbicide of the present invention, the compound of the present invention is contained in a range of usually 0.1 to 80% by weight.

Examples of the solid carrier include fine powders or granules of clays (for example, kaolin clay, diatomaceous earth, synthetic hydrated silicon oxides, Fubasami clay, bentonite, or acid white clay), talcs, other inorganic minerals (for example, sericite, quartz powders, sulfur powders, active carbon, calcium carbonate or hydrated silica). Examples of the liquid carrier include water; alcohols (for example, methanol or ethanol); ketones (for example, acetone or methyl ethyl ketone); aromatic, hydrocarbons (for example, toluene, xylene, ethyl benzene, or methylnaphthalene); aliphatic hydrocarbons (for example, n-hexane, cyclohexane or kerosene); esters (for example, ethyl acetate or butyl acetate); nitriles (for example, acetonitrile or isobutyronitrile), ethers (for example, diisopropyl ether); and amides (for example, dimethylformamide or dimethylacetamide).

Examples of the surfactants include alkyl sulfates, alkyl sulfonates, alkyl aryl sulfonates, alkyl aryl ethers and polyoxyethylenated compounds thereof, polyoxyethylene glycol ethers, polybydric alcohol esters, and sugar alcohol derivatives.

Examples of the other auxiliary agents for formulation include a binder and a dispersant. Specific examples include casein, gelatin, polysaccharides (for example, starch, gum arable, cellulose derivatives or alginic acid), lignin derivatives, bentonite, sugars, water-soluble synthetic polymers (for example, polyvinyl alcohol, polyvinyl pyrrolidone or polyacrylic acids), PAP (acidic isopropylphosphate) BHT (2,6-di-tert-butyl-4-methylphenol), BHA (a mixture of 2-tert-butyl-4-methoxyphenol and 3-tert-butyl-4-methoxyphenol), plant oil, mineral oil, fatty acid and the others.

A method for controlling weeds of the present invention comprises a step of applying an effective amount of a compound of the present invention to weeds or soil where weeds are growing or will grow. In the method for controlling weeds of the present invention, usually, the compound of the present invention is used as a herbicide of the present invention.

Examples of the method of applying the compound of the present invention include a method of applying the present compound to stems and leaves of weeds, a method of applying the present compound to a surface of soil where weeds are growing or will grow, a method of incorporating the present compound into soil where weeds are growing, and a method of applying the present compound to a surface water of paddy field that an area where weeds are growing or will grow is flooded.

Examples of the weeds which can be controlled by the present compound include the following weeds, but are not limited thereto.

Urticaceae weeds: *Urtica urens;*

Polygonaceae weeds: *Polygonum convolvulus, Polygonum lapathifolium, Polygonum pensylvanicum, Polygonum persicaria, Polygonum longisetum, Polygonum aviculare, Polygonum, arenastrum, Polygonum cuspldatum, Rumex japonicus, Rumex crispus, Rumex obtusifolius,* and *Rumex acetosa;*

Portulacaceae weeds: *Portulaca oleracea;*

Caryophyllaceae weeds: *Stellaria media, Stellaria aquatics, Cerastium holosteoldes, Cerastium glomeraturn, Spergula arvensis,* and *Silene gallica;*

Molluginaceae weeds: *Mollugo verticlllata;*

Chenopodiaceae weeds: *Chenopodium, album, Chenopodlum ambrosioides, Kochia scoparia, Salsola kali,* and *Atriplex* spp;

Amaranthaceae weeds: *Amaranthus retroflexus, Amaranthus viridis, Amaranthus livldus, Amaranthus spinosus, Amaranthus hybridus, Amaranthus palmeri, Amaranthus rudis, Amaranthus patulus, Amaranthus tuberculatos, Amaranthus hlltoides, Amaranthus deflexus, Amaranthus quitensis, Altarnanthera philoxeroides, Alternanthera sessilis,* and *Alternanthera tenella;*

Papaveraceae weeds: *Papaver rhoeas,* and *Argemone mexicana;*

Brassicaceae weeds: *Raphanus raphanistrum, Raphanus sativus, Sinapis arvensis, Capsella bursa-pastoris, Brassica juncea, Brassica campestris, Descurainia pinnata, Rorippa islandica, Rorippa sylvestris, Thlaspi arvense, Myagrum rugosum, Lepidium virginicum, Coronopus didymvs,* and *Arabidopsis thaliana;*

Capparaceae weeds: *Cleome affinis;*

Fabaceae weeds: *Aeschynomene indica, Aeschynomene rudis), Sesbania exaltata, Cassia obtusifolia, Cassia occidentalis, Desmodium tortuosum, Desmodium adscendens, Desmodium illinoense, Trifolium repens, Pueraria lobata, Vicia angustifolia, Indigofera hirsuta, Indigofera truxiliens is,* and *Vigna sinensis;*

Oxalidaceae weeds: *Oxalis corniculata, Oxalis strica,* and *Oxalis oxyptera;*

Geraniaceae weeds: *Geranium caroiinense,* and *Erodium cicutar ium;*

Euphorbiaceae weeds: *Euphorbia: helioscopia, Euphorbia maculata, Euphorbia humistrata, Euphorbia esula, Euphorbia heterophylla, Euphorbia brasiliensis, Acalypha australis, Croton glandulosus, Croton lobatus, Phyllanthus corcovadensis,* and *Ricinus communis;*

Malvaceae weeds: *Abutilion theophrasti, Sida rhombifo-ria, Sida cordifolia, Sida spinosa, Sida glaziovii, Sida santaremnensis, Hibiscus trionum, Anoda cristata,* and *Malvastrum coromandelianum;*

Onagraceae weeds: *Ludwigia epilobioides, Ludwigia octovalvis, Ludwigia decurre, Oenothera biennis,* and *Oenothera laciniata;*

Sterculiaceae weeds: *Waltheria indica;*

Violaceae weeds: *Viola arvensis,* and *Viola tricolor;*

Cucurbitaceae weeds: *Sicyos angulatus, Echinocystis lobata,* and *Momordica charantia;*

Lythraceae weeds: *Ammannia multiflora, Ammannia auriculata, Ammannia coccinea, Lythrum salicaria,* and *Rotala indica;*

Elatinaceae weeds: *Elatine triandra,* and *Elatine californ-ia;*

Apiaceae weeds: *Oenanthe javanica, Daucus carota,* and *Conium maculatum;*

Araliaceae weeds: *Hydrocotyle sibthorpioides,* and *Hydrocotyle ranunculcides;*

Ceratophyllaceae weeds: *Ceratophyllum demersum;*

Cabombaceae weeds: *Cabomba caroliniana;*

Haloragaceae weeds: *Myriophyllum aquaticum, Myriophylluro verticillatum,* and Water-milfoils (for example, *Myriophyllum sulcatum,* and *Myriophyllum heterophyllum*);

Sapindaceae weeds: *Cardiospermum halicacabum;*

Primulaceae weeds: *Anagallis azvensis;*

Asclepiadaceae weeds: *Asclepias syriaca,* and *Ampelamus albidus;*

Rubiaceae weeds: Galium sparine, Galium spurium var. echinospermon, Spermacoce latifolia, Richardia brasiliensis, and *Borreria alata;*

Convolvulaceae weeds: Ipomoea nil, Ipomoea hederacea, Ipomoea purpurea, Ipomoea hederacea var. integriuscula, Ipomoea lacunosa, Ipomoea triloba, Ipomoea acuminata, Ipomoea hederifolia, Ipomoea coccinea, Ipomoea quamoclit, Ipomoea grandfolia, Ipomoea aristolochiafolia, Ipomoea cairica, Convolvulus arvensis, Calystegia hederacea, Calystegia japonica, Merremia hedeacea, Merremia aegyptia, Merremia cissoides, and *Jacquemontia tamnifolia;*

Boraginaceae weeds: *Myosotis arvensis;*

Lamiaceae weeds: *Lamium pvrpureum, Lamium amplexicaule, leonotis nepetaefolia, Hyptis suaveolens, Hyptis lophanta, Leonurus sibiricus,* and *Stachys arvensis;*

Solanaceae weeds: *Datura stramonium, Solanum nigrum, Solatium americanum, Solanum ptycanthum, Solanum sarrachoides, Solanum rostratum, Solanum aculeatissimum, Solanum sisymbri ifolium, Solanum carolinense, Physalis angulata, Physalis subglabrata,* and *Nicandra physaloides;*

Scrophulariaceae weeds: *Veronica hederaefolia, Veronica persica, Veronica arvensis, Lindernia procumbens, Lindernia dubia, Lindernia angustifolia, Bacopa rotundifolia, Dopatrium junceum,* and *Gratiola japonica;*

Plantaginaceae weeds: *Plantago asiatica, Plantago lanceolata, Plantago major,* and *Callitriche palustris;*

Asteraceae weeds: *Xanthium pensylvanicum, Xanthium occidentale, Xanthium italicum, Helianthus annuus, Matricaria chamomilla, Matricaria perforata, Chrysanthemum segetum, Matricaria matricarioides, Artemisia princeps, Artemisia vulgaris, Artemisia verlotorum, Solidago altissima, Taraxacum officinale, Galinsoga ciliata, Galinsoga parviflora, Senecio vulgaris, Senecio brasiliensis, Senecio grisebachii, Conyza bonariensis, Conyza canadensis, Ambrosia artemisiae folia, Ambrosia, trifida, Bidens tripartita, Bidens pilosa, Bidens frondosa, Bidens subalternans, Cirsium arvense, Cirsium vulgare, Silybum marianum, Cardvus nutans, Lactuca serriola, Sonchus ciaraceus, Sonchus asper, Wedelia glauca, Melampodium perfolialum, Emilia sonchifolia, Tagetas minuta, Blainvillea lati folia, Tridax procumbens, Porophyllum ruderale, Acanthospermum australe, Acanthospermum hispidum, Cacdiospermum halicacabum, Agerafurn conyzoides, Eupatorium perfoliatum, Eclipta alba, Erechtites hieracifolia, Gamochaeta spicata, Gnaphalium spicatum, Jaegeria hirta, Parthenium hysterophorus, Siegesbeckia orientalis, Soliva sessilis, Eclipta prostrata, Eclipta alba,* and *Centipeda minima;*

Alismataceae weeds: *Sagittaria pygmaea, Sagittaria tri-folia, Sagittaria sagittifolia, Sagittaria montevidensis, Sagittaria aginashi, Alisma canaliculatum,* and *Alisma plantago-aquatica;*

Limnocharitaceae weeds: *Limnocharis flava;*

Hydrocharitaceae weeds: *Limnobium spongia, Hydrilla verticillata,* and *Najas guaclalupensis;*

Araceae weeds: *Pistia stratiotes;*

Leranaceae weeds: *Lemna aoukikusa, Spirodela polyrhiza,* and *Wolffia* spp;

Potamogetonaceae weeds: *Potamogeton distinctus,* and pond weeds (for example, *Potamogeton crispus, Potamogeton illinoensis,* and *Stuckenia pectinata*);

Liliaceae weeds: *Allium canadense, Allium vineale,* and *Allium macrostemon;*

Pontederiaceae weeds: *Eichhornia crassipes, Heteranthera limosa, Monochorea korsakowii,* and *Monochorea vaginalis;*

Commelinaceae weeds: *Commelina communis, Commelina bengharensis, Commelina erecta,* and *Murdannia keisak;*

Poaceae weeds: *Echinochloa crus-galli, Echinochloa oryzicola, Echinochloa crus*-galli var formosensis, Echinochloa oryzoides, Echinochloa colona, Echinochloa crus-*pavonis, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Poa trivialis, Poa pratensis, Aiospecurus aequalis, Alopecurus myosuroides, Avena fatua, Sorghum halepense, Sorghum vulgare, Agropyron repens, Lolium perenne, Lolium rigidum, Bromus catharticus, Bromus sterilis, Bromus japonicus, Bromus secalinus, Bromus tectcrum, Hordeum jubatum, Aegilops cylindrical Phalaris arundinacea, Phalaris minor, Apera spica-venti, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Eragrostis piiosa, Rhynchelitrum repens, Dactyloctenium aegyptium, Ischaemum rugosum, Isachne globosa, Oryza sativa, Paspalum notatum, Paspalum maritimum, Paspalum distichum, Pennisetum clandestinum, Pennisetum setosum, Roctboellia cochinchinensis, Leptochloa chinensis, Leptochloa fascicularis, Leptochloa filiformis, Leptochloa panicoides, Leersia japonica, Leersia sayanuka, Leersia oryzoides, Glyceria leptorrhiza, Glyceria acutiflora, Glyceria maxima, Agrostis stolonifera, Cynodon dactylon, Dactylis glomerata, Eremochloa ophiuroides, Festuca arundinacea, Festuca rubra, Imperata cylindricar Miscanthus sinensis, Panicum virgatum,* and *Zoysia japonica;*

Cyperaceae weeds: *Cyperus microiria, Cyperus iria, Cyperus compressus, Cyperus difformis, Cyperus flaccidus, Cyperus globosus, Cyperus nipponics, Cyperus odoratus, Cyperus serotinus, Cyperus rotundus, Cyperus esculentus, Kyllinga gracillima, Kyllinga brevifolia, Fimbristylis miliacea, Fimbristylis dichotoma, Eleocharis acicularis, Eleocharis kuroguwai, Schoenoplectus hotarui, Schoenoplectus juncoides, Schoenoplectus wallichii, Schoenoplectus mucronatus, Schoenoplectus triangulatus, Schoenoplectus nipponicus, Schoenoplectus triqueter, Bolboschoenus koshevnikovii,* and *Bolboschoenus fluviatilis;*

Equisetaceae weeds: *Equisetum arvense,* and *Equisetum*

Salviniaceae weeds: *Salvinia natans;*

Azollaceae weeds: *Azolla japonica,* and *Azolla imbricata;*

Marsileaceae weeds: *Marsilea quadrifolia;* and

Other weeds: filamentous algae (for example, Pithophora, Cladophora), mosess, liverwort, hornwort, cyanobacteria, bracken, and sucker of parmanent crops (for example, pome fruits, stone fruits, berry fruits, nut fruit, citrus fruit, hop, grapes, and the others),

EXAMPLES

Hereinafter, the present invention is explained in more detail by using Preparation Example and Test Example, however, the present invention should not be limited to these examples.

First, the Preparation Examples are shown.

Preparation Example 1

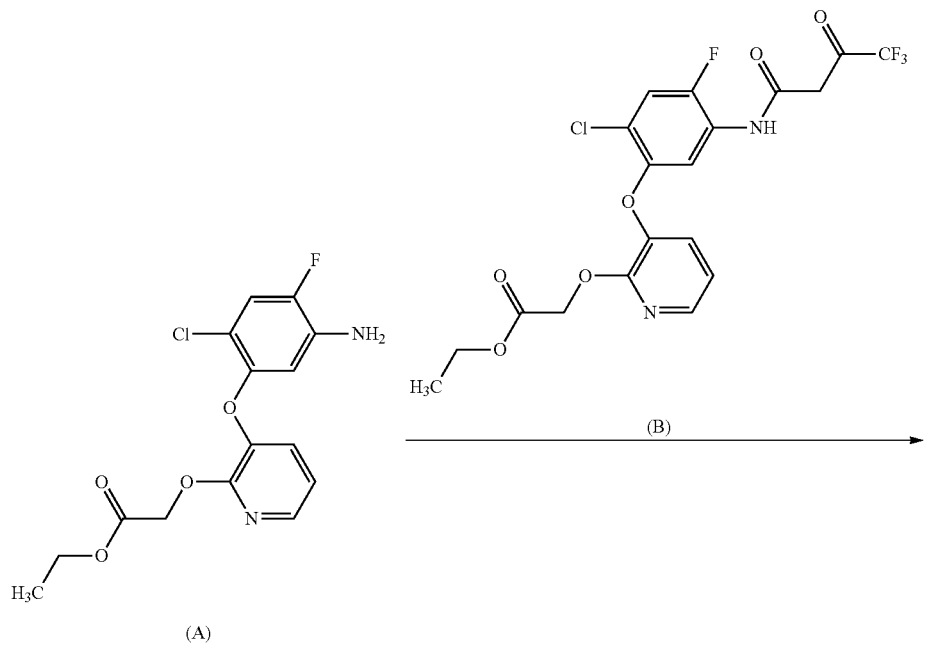

-continued

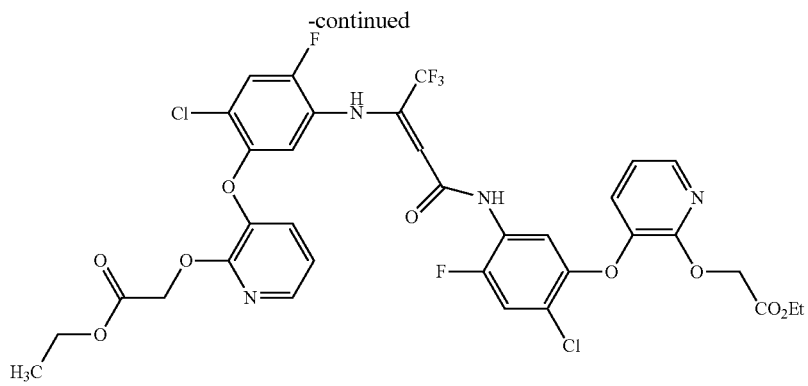

A mixture of 0.14 g of a compound represented by the above-mentioned formula (A) (descried in JP patent No. 4356247; hereinafter, referred to as Compound A), 0.20 g of a compound represented by the above-mentioned formula (B) (described in JP patent No. 4356247; hereinafter, referred to as Compound B), 8.0 mg of p-toluenesulfonic acid monohydrate, and 10 mL of toluene was stirred under reflux for 2 hours using Dean-Stark trap. The mixture was cooled to room temperature, and concentrated under reduced, pressure. The residues were purified by a preparative thin layer chromatography to give 0.14 g of the present compound. $^1$H-NMR (CDCl$_3$): δ(ppm): 10.14 (1H, s), 8.07 (1H, s), 7.90 (1H, dd, J=4.9, 1.6 Hz), 7.85 (1H, dd, J=4.9, 1.6 Hz), 7.23 (1H, d, J=2.7 Hz), 7.14-7.04 (3H, m), 6.91-6.84 (4H, m), 5.37 (1H, s), 4.95 (2H, s), 4.92 (2H, s), 4.25-4.16 (4H, m), 1.29-1.20 (6H, m). ESI-MS (posi): 801 [M+H]$^+$ ESI-MS (nega): 799 [M-H]$^-$ Next, Test examples are shown below.

Test Example 1: Post-emergence treatment test in a farmland

Nursery soil was put in a plastic pot measuring 8 cm in diameter and 6.5 cm in height, and in the pot, seeds of *Amaranthus retroflexus* were sown, and then covered with soil of about 0.5 cm thickness, and the plants were grown in a greenhouse. When the *Amaranthus retroflexus* plants were grown to two-leaf stage, a diluted solution containing any one of the present compound, the compound A, or the compound B was uniformly sprayed on the whole *Amaranthus retroflexus* plants so that the application rates of the chemicals would be values indicated in Table 1.

Here the diluted solution was prepared by dissolving the present compound, the compound A, or the compound B in dimethylformamide solution containing 2% of Tween 20 (polyoxyethylene sorbitan fatty acid ester) (manufactured by MP Biomedicals Inc.) and then diluting the solution with deionized water.

The *Amaranthus retroflexus* plants that were sprayed with the diluted solution containing the present compound, the compound A, or the compound B were grown in a greenhouse. Nine clays after spraying, the efficacy for controlling *Amaranthus retroflexus* plants was observed, thereby examining a herbicidal effect. Here the herbicidal effect was visually observed and evaluated by classifying the effect into 11 stages from 0 (no effect) to 10 (complete kill). The results are shown in Table 1.

The results showed that the present compound showed higher herbicidal effect compared to the compound A or the compound B.

TABLE 1

|  | Application rates of the Chemicals (kg/ha) | Herbicidal Effect |
| --- | --- | --- |
| Present compound | 4 | 8 |
| Compound A | 4 | 1 |
| Compound B | 4 | 3 |

Test Example 2

Herbicidal effect against *Echinochloa oryzicola* and *Lindernia procumbens* (Pot test in greenhouse)

Soil was put in a plastic pot (φ 5 cm×5.5 cm), and soil was puddled, and the plastic pot was allowed to stand for 2 days, *Lindernia procumbens* seeds were mixed with soil, and sown to the surface of puddled soil in the pot. On the same day, the sprouted seeds of *Echinochloa oryzicola* were sown into about 0.5 cm depth from the soil surface of the pot, and the submerged depth was adjusted to about 2 cm.

Treatment solutions containing the present, compound, the compound A, or the compound B were prepared by dissolving the present compound, the compound A, or the compound B in acetone, followed by diluting the resulting solutions with distilled water. On the same day as the sowing of *Echinochloa oryzicola* and *Lindernia procumbens*, the treatment solution containing the present compound, the compound A, or the compound B was poured into paddy water in the pot so that the application rates of the chemicals would be values indicated in Table 2.

Twelve days after the treatment, the herbicidal effect on weeds was visually observed by classifying the effect into 0 to 100 indices (0 (no effect) to 100 (complete kill)). The results are shown in Table 2.

The results showed that the present compound showed higher herbicidal effect compared to the compound A or the compound B.

TABLE 2

|  |  | Herbicidal Effect | |
| --- | --- | --- | --- |
|  | Application rates (g/a) | *Echinochloa oryzicola* | *Lindernia procumbens* |
| Present compound | 100 | 100 | 60 |
|  | 50 | 100 | 50 |
| Compound A | 100 | 10 | 0 |
|  | 50 | 0 | 0 |
| Compound B | 100 | 0 | 0 |
|  | 50 | 0 | 0 |

Test Example 3: Hydroponic Test of *Echinochloa oryzicola*

Two (2) mL of distilled water was poured into a plastic tube (2.5 cm in inside diameter×10 cm in height). To the distilled water was added a solution in which the present compound or the compound A was dissolved in dimethyl sulfoxide to prepare the treatment solutions so that, the treatment concentration thereof would be values indicated in table 3. Next, four grains of sprouted *Echinochloa oryzicola* seeds were put in each treatment solution. The tubes were covered with parafilm, and the seeds were grown under the condition that a cultivation at 25° C. under lightning for 16 hours and a successive cultivation at 25° C. under dark for 8 hours were repeated. Ten days after the addition of the *Echinochloa oryzicola* seeds, the herbicidal effect on *Echinochloa oryzicola* was visually observed by classifying the effect into 0 to 100 indices (0 (no effect) to 100 (complete kill)). The results are shown in Table 3, The results showed that the present compound showed higher herbicidal effect compared to the compound A.

TABLE 3

|  | Treatment Concentration (ppm) | Herbicidal Effect |
| --- | --- | --- |
| Present compound | 500 | 100 |
|  | 250 | 100 |
|  | 125 | 100 |
| Compound A | 500 | 0 |
|  | 250 | 0 |
|  | 125 | 0 |

Test Example 4: Inhibitory Activity on Emergence of *Arabidopsis thaliana*

Each well of 24 well microtiter plates was matted with a filter paper, and to the filter paper was added 150 μL of distilled water. To the distilled water was added a solution in which the present compound, the compound A, or the compound B was dissolved in dimethyl sulfoxide so that the concentration of each of the chemicals would be values indicated in Table 4. Next, seeds of Arabidopsis thaliana were sown into each well and grown under the condition that a cultivation at 25° C. under lighting for 16 hours and a successive cultivation at 25° C. under dark for 8 hours were repeated. Ten days after sowing, the inhibitory activity on emergence of Arabidopsis thaliana was visually evaluated by classifying the activity into 0 to 100 indices (0: no effect to 100: no emergence). The results are shown in Table 4.

The results showed that the present compound showed higher inhibitory activity compared to the compound A or the compound B.

TABLE 4

|  | Treatment Concentration (ppm) | Inhibitory Activity on Emergence |
| --- | --- | --- |
| Present compound | 1000 | 100 |
|  | 500 | 100 |
| Compound A | 1000 | 0 |
|  | 500 | 0 |
| Compound B | 1000 | 0 |
|  | 500 | 0 |

INDUSTRIAL APPLICABILITY

The compound of the present invention has excellent efficacies for controlling weeds, and is useful as an active ingredient for an agent for controlling weeds.

The invention claimed is:

1. A compound represented by formula (1):

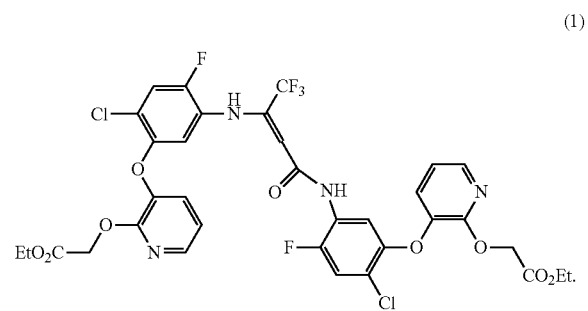 [SMILES: CCOC(=O)COc1ncccc1Oc1cc(NC(=O)C=C(Nc2cc(Oc3cccnc3OCC(=O)OCC)c(Cl)cc2F)C(F)(F)F)c(F)cc1Cl]

(1)

2. A herbicide formulation comprising the compound according to claim 1.

3. A method for controlling a weed which comprises applying the compound according to claim 1 to the weed or soil where the weed is growing.

* * * * *